United States Patent [19]
Corn et al.

[11] Patent Number: 6,127,129
[45] Date of Patent: Oct. 3, 2000

[54] PROCESS TO CREATE BIOMOLECULE AND/OR CELLULAR ARRAYS ON METAL SURFACES AND PRODUCT PRODUCED THEREBY

[75] Inventors: Robert M. Corn, Madison, Wis.; Anthony G. Frutos, Big Flats, N.Y.; Jennifer M. Brockman, Madison, Wis.

[73] Assignee: Wisconsin Alumni Research Foundation, Madison, Wis.

[21] Appl. No.: 09/368,991

[22] Filed: Aug. 5, 1999

Related U.S. Application Data

[60] Provisional application No. 60/132,342, May 4, 1999.

[51] Int. Cl.[7] .............................. C12Q 1/68; G03F 9/00
[52] U.S. Cl. ..................................... 435/6; 430/5
[58] Field of Search ...................... 435/6; 430/5

[56] References Cited

U.S. PATENT DOCUMENTS

| | | |
|---|---|---|
| 5,242,828 | 9/1993 | Bergström et al. . |
| 5,347,395 | 9/1994 | Lautenschlager et al. . |
| 5,359,681 | 10/1994 | Jorgenson et al. . |
| 5,374,563 | 12/1994 | Maule . |
| 5,418,136 | 5/1995 | Miller et al. . |
| 5,436,161 | 7/1995 | Bergström et al. . |
| 5,468,606 | 11/1995 | Bogart et al. . |
| 5,482,830 | 1/1996 | Bogart et al. . |
| 5,492,840 | 2/1996 | Malmqvist et al. . |
| 5,494,829 | 2/1996 | Sandstrom et al. . |
| 5,514,501 | 5/1996 | Tarlov ........................................ 430/6 |
| 5,541,057 | 7/1996 | Bogart et al. . |
| 5,550,063 | 8/1996 | Bogart . |
| 5,552,272 | 9/1996 | Bogart . |
| 5,554,541 | 9/1996 | Malmqvist et al. . |
| 5,583,643 | 12/1996 | Gass et al. . |
| 5,629,213 | 5/1997 | Kornguth et al. . |
| 5,629,214 | 5/1997 | Crosby . |
| 5,631,171 | 5/1997 | Sandstrom et al. . |
| 5,639,671 | 6/1997 | Bogart et al. . |
| 5,647,030 | 7/1997 | Jorsenson et al. . |
| 5,688,642 | 11/1997 | Chrisey et al. ............................ 435/6 |
| 5,815,278 | 9/1998 | Johnston et al. . |
| 5,822,073 | 10/1998 | Yee et al. . |
| 5,835,645 | 11/1998 | Jorgenson et al. . |
| 5,858,799 | 1/1999 | Yee et al. . |
| 5,869,272 | 2/1999 | Bogart et al. . |

FOREIGN PATENT DOCUMENTS 0 305 108  1/1989  European Pat. Off. .

OTHER PUBLICATIONS

Pale–Grosdemage et al., "Formation of Self–Assembled Monolayers by Chemisorption of Derivatives of Oligo(ethylene glycol) of Structure HS(CH2)11(oCH2CH2)mOH on Gold" J. Am. Chem. Soc. 113, pp. 12–20, 1991.

Brockman et al., "A Multistep Chemical Modification Procedure to Create DNA Arrays on Gold Surfaces for the Study of Protein–DNA Interactions with Surface Plasmon Resonance Imaging" J. Am. Chem. Soc. 121, pp. 8044–8051, 1999.

Frutos, A. G. et al, "Demonstration of a Word Design Strategy for DNA Computing on Surfaces," *Nucleic Acids Research* 25:4748–4757 (1997).

Frutos, A. G. et al, "Enzymatic Ligation Reactions of DNA "Words" on Surfaces for DNA Computing," *J. Am. Chem. Soc.* 120:102777–10282 (1998).

Gross, C. A. et al, "Application of (3–Mercaptopropyl)trimethoxysilane as a Molecular Adhesive in the Fabrication of Vapor–Deposited Gold Electrodes on Glass Substrates," *Anal. Chem.* 63:85–88 (1991).

Jordon, C. E. et al, "Surface Plasmon Resonance Imaging Measurements of Electrostatic Biopolymer Adsorption onto Chemically Modified Gold Surfaces," *Anal. Chem.* 69:1449–1456 (1997).

Jordan, C. E. et al, "Surface Plasmon Resonance Imaging Measurements of DNA Hybridization Adsorption and Streptavidin/DNA Multilayer Formation at Chemically Modified Gold Surfaces," *Anal. Chem.* 69:4939–4947 (1997).

Knobloch, H. et al, "Dispersive Surface Plasmon Microscopy for the Characterization of Ultrathin Organic Films," *Appl. Phys. Lett.* 69:2336–2337 (1996).

Lideberg, B. et al, Surface Plasmon Resonance for Gas Detection and Biosensing, *Sensors and Actuators*, 4:299–304 (1983).

Pease, A. C. et al, "Light–Generated Oligonucleotide Arrays for Rapid DNA Sequence Analysis," *Proc. Natl. Acad. Sci.* 91:5022–5026 (1994).

Thiel, A. J., et al, "In Situ Surface Plasmon Resonance Imaging Detection of DNA Hybridization to Oligonucleotide Arrays on Gold Surfaces," *Anal. Chem.* 69:4948–4956 (1997).

Thomas, R. C. et al, "Probing Adhesion Forces at the Molecular Scale," *J. Am. Chem. Soc.* 117:3830–3834 (1995).

Winzeler, E. A. et al, "Direct Allelic Variation Scanning of the Yeast Genome," *Science* 281:1194–1197 (1998).

Zizlsperger, M. et al, "Multispot Parallel On–Line Monitoring of Interfacial Binding Reactions by Surface Plasmon Microscopy," *Progr. Colloid. Polym. Sci.* 109:244–253 (1998).

*Primary Examiner*—Eggerton A. Campbell
*Assistant Examiner*—Jeffrey S Lundgen
*Attorney, Agent, or Firm*—DeWitt Ross & Stevens S.C.

[57] ABSTRACT

Disclosed is a process to construct multi-component biomolecule or cellular arrays suitable for use in SPR imaging studies of large molecule, cellular/molecular, and cell/cell interactions. The success of the procedure hinges on the use of a reversible protecting group to modify reversibly ω-functionalized alkanethiols self-assembled on metal substrates.

25 Claims, 7 Drawing Sheets

PROCESS TO CREATE BIOMOLECULE AND/OR CELLULAR ARRAYS ON METAL SURFACES AND PRODUCT PRODUCED THEREBY

CROSS-REFERENCE TO RELATED APPLICATIONS

This application claims priority under 35 USC §119(e) to U.S. Provisional Patent Application 60/132,342 filed on May 4, 1999, the entirety of which is incorporated by reference herein.

FIELD OF THE INVENTION

The invention is directed to the fabrication of biomolecular or cellular arrays on metal surfaces for use in the study of interactions between large molecules, between cells and large molecules, and between cells, such as nucleic acid-protein interactions or cellular interactions with antigens.

DESCRIPTION OF THE PRIOR ART

The binding of proteins to DNA plays a pivotal role in the regulation and control of gene expression, replication and recombination. In addition, enzymes that recognize and modify specific oligonucleotide sequences are critical components of biological nucleic acid manipulation and repair systems. An enhanced understanding of how these proteins recognize certain oligonucleotide sequences would aid in the design of biomedical systems which could, for example, be used to regulate the expression of therapeutic proteins. For this reason, the study of protein-nucleic acid interactions (i.e., protein-DNA and protein-RNA interactions) is a rapidly growing area of molecular biology, aided in part by recent advances in NMR and X-ray structural determination methods. At the same time, the explosive increase in the amount of available genomic and extra-genomic (i.e., ribosomal) sequence information obtained from large-scale nucleic acid sequencing efforts creates a need to survey this vast amount of new sequence data for protein binding sites. The present invention addresses this need by using surface plasmon resonance (SPR) imaging techniques as a rapid and efficient method for screening the sequence or structure-specific binding of proteins to large arrays of nucleic acid molecules immobilized at chemically-modified metal surfaces.

Arrays of DNA molecules attached to planar surfaces are currently employed in hybridization adsorption experiments to sequence DNA, Pease et al. (1994) *Proc. Natl. Acd. Sci. USA* 91:5022–5026; to screen for genetic mutations, Winzeler et al. (1998) *Science* 281:1194–1197: and in DNA computing applications, Frutos et al. (1997) *Nucleic Acids Res.* 25:4748–4757; and Frutos et al (1998) *J Am. Chem. Soc.* 120:10277–10282. These arrays are exposed to solutions containing fluorescently labeled complementary DNA sequences, rinsed, and then "read-out" using fluorescence imaging methods.

The technique of surface plasmon resonance (SPR) is a surface-sensitive, optical detection method well suited to the monitoring of reversible, protein-nucleic acid interactions. The commercially successful "BIAcore" SPR instrument (Biacore AB, Uppsala, Sweden) has been used previously, for example, to study the interaction of DNA molecules with various enzymes. Although powerful, the "BIAcore" instrument has no imaging capabilities. This severely limits the number of DNA sequences that can be screened in a single experiment.

Surface plasmon resonance (SPR) is a surface optical technique which is sensitive to the thickness and index of refraction of material at the interface between a free electron metal (e.g. gold, silver, copper, cadmium, aluminum) and a bulk medium, such as air or water. Surface plasmon resonance may be achieved by using the evanescent wave which is generated when a laser beam linearly polarized parallel to the plane of incidence impinges onto a prism coated with a thin metal film. The metal may also be coated onto a thin transparent substrate such as glass, and this glass brought into optical contact with the prism. SPR is most easily observed as a reduction of the total internally reflected light just past the critical angle of the prism. This angle of minimum reflectivity (denoted as the SPR angle) shifts to higher angles as material is adsorbed onto the metal layer. The shift in the angle can be converted to a measure of the thickness of the adsorbed or added material by using complex Fresnel calculations and can be used to detect the presence or absence of materials on top of the metal layer.

In using SPR to test for biological, biochemical, or chemical substances, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical, or chemical substance. The organic film can contain substances, such as antibodies or antigens, which can bind with an analyte in a sample to cause an increased thickness which will shift the SPR angle. By monitoring either the position of the SPR angle or the reflectivity at a fixed angle near the SPR angle, the presence or absence of an analyte in the sample can be detected. Various types of equipment for using SPR with a biosensor for biological or biochemical or chemical substances are described by the Liedberg et al. article found in "Sensors and Actuators," Vol. 4, 1983, page 299. See also European Patent Application 0 305 108 and U.S. Pat. No. 5, 374, 563.

The use of conventional SPR as a testing tool offers several advantages and disadvantages. For example, it is relatively fast, it requires no labeling, and it can be performed on site. However, as noted above, commercially-available devices, such as the "BIAcore" instrument, offer no imaging capabilities. Additionally, to achieve the high through-put demanded by large-scale users, there is a need for a simple, practical biosensor which can be readily modified or adapted to test a wide variety of compounds simultaneously.

In SPR imaging, a light source (typically a HeNe laser) is used to illuminate a prism/thin gold film sample assembly at an incident angle that is near the SPR angle, and the reflected light is detected at a fixed angle with a CCD camera to produce an SPR image. The SPR image arises from variations in the reflected light intensity from different parts of the sample; these variations are created by any changes in organic film thickness or index of refraction that occur upon adsorption onto the modified gold surface. Since SPR imaging is sensitive only to molecules in close proximity to the surface (within~200 nm), unbound molecules remaining in solution do not interfere with in situ measurements.

The formation of robust, reproducible arrays of oligo-nucleotides tethered to metal-coated surfaces (most often gold) is an essential requirement for SPR imaging of protein-nucleic acid binding interactions. To use SPR imaging techniques, it is essential that the nucleic acid array be constructed on a noble metal surface, and for this reason DNA arrays on glass supports from commercially available sources such as Affymetrix (Santa Clara, Calif.) are not a viable option. Using self-assembled monolayers of substituted alkanethiols as a starting point, others have previously developed schemes to attach single-stranded DNA molecules to chemically modified gold surfaces. See, for instance, U.S. Pat. No. 5, 629,213). In the subject invention, however, UV photopatterning and microcontact printing techniques are brought to bear to allow alkanethiols to be assembled in a site-directed manner on the metal surface, thereby enabling the creation of multi-component arrays. A combination of these processing techniques along with novel surface chemical reactions enables the manufacture of nucleic acid arrays as described herein.

SUMMARY OF THE INVENTION

Disclosed is a multi-step chemical modification procedure to create biomolecule and/or cellular arrays on metal substrates, the arrays being specifically tailored for the study of biomolecular and cellular interactions using surface plasmon resonance imaging. Arrays fabricated by this procedure meet three specific requirements, namely (i) the biomolecules are covalently attached to the surface and remain active and accessible to hybridization and protein binding; (ii) the array background is, at first, sufficiently hydrophobic so as to allow for the "pinning" of aqueous solutions of biomolecules or cells at specific array locations; and (iii) the final array background acts to inhibit the non-specific binding of protein molecules to the surface. The key components of this fabrication scheme are the utilization of a reversible hydrophobic protecting group, preferably Fmoc, to control the surface hydrophobicity of a tethered ω-modified alkanethiol monolayer and the attachment of a poly(ethylene glycol) (PEG) group to render the surface protein resistant. Polarization-modulation Fourier Transform infrared (PM-FTIR) spectroscopy, contact angle, and SPR measurements are used to characterize each step in the surface modification procedure and confirm that the array background inhibits the non-specific binding of proteins. As a final test, an SPR imaging experiment which measures the adsorption of single-stranded DNA binding protein (SSB) to a dual component, oligonucleotide array demonstrates the utility of these surfaces for the monitoring of protein-nucleic acid interactions.

The multi-step procedure disclosed herein is used to create an array of spots that are surrounded first by a hydrophobic background which allows for the pinning of aqueous biomolecule or cell solutions onto individual array elements and then to replace the hydrophobic background with one that resists the non-specific adsorption of proteins during in situ SPR imaging measurements, thereby yielding an array of biomolecule or cell "islands" in a "sea" which resists non-specific adsorption of proteins.

In the preferred embodiment, amine-terminated alkanethiol monolayers are employed as the base layer, and Fmoc and PEG modifiers are used to create the sequentially hydrophobic and protein adsorption-resistant surfaces, respectively. In the preferred embodiment, the chemical modification steps are: (i) the adsorption and self-assembly of an 11-mercaptoundecylamine (MUAM) monolayer on an evaporated gold thin film; (ii) the reaction of the MUAM monolayer with an Fmoc protecting group to create a hydrophobic surface; (iii) the photopatterned removal of the alkanethiol followed by (iv) the re-adsorption of MUAM to create an array of MUAM squares (approximately 750 $\mu$m×750 $\mu$m, although smaller or larger squares are attainable) surrounded by a hydrophobic MUAM-Fmoc background that can pin drops of aqueous solution; (v) the attachment of oligonucleotide sequences onto the MUAM squares by the reaction of the amine-terminated surface with the heterobifunctional cross-linker (preferably SSMCC), followed by a coupling reaction to a small volume (0.1 $\mu$L) of thiol-modified DNA; (vi) the removal of the Fmoc protecting group followed by (vii) a pegylation reaction of the MUAM with PEG-NHS to create a protein adsorption-resistant background.

A combination of polarization-modulation FTIR spectroscopy, contact angle and scanning angle SPR measurements are used to characterize the surface modification procedure. An SPR imaging measurement of the adsorption of single-stranded DNA binding protein (SSB) onto an oligonucleotide array created by this procedure is used to demonstrate the utility of these surfaces to probe nucleic acid interactions with protein and other analytes.

A primary advantage of the subject invention is that it allows an array of immobilized biomolecules or cells to be constructed in which each "island" of bound molecules or cells may differ from the other islands in the array. This allows for massive and simultaneous analysis of a tremendous number of different molecules or cells for their individual affinities and/or binding characteristics to a selected analyte. The fabrication method described herein is well-suited to automation and SPR experiemnts can be analyzed using standard-format microtiter plates and lab automation equipment (i.e., 96-well, 384-well, and larger formats).

The arrays described herein are useful for any number of analyses wherein a biomolecule or cell interacts with a protein, antigen, or some other molecule, such as in determining binding affinities, epitope mapping, restriction site mapping, measuring the binding effects of short-range secondary structure in nucleic acids, etc. For example, by building an array wherein islands of nucleic acids differ systematically, as by length or primary sequence, the interactions of any given nucleic acid sequence for any given analyte can be quickly and exhaustively investigated. Likewise, the effects of short-range secondary structure in nucleic acids can be investigated by building an array wherein the islands of nucleic acids differ in sequence such that the islands contain nucleic acid sequences which progressively contain more stable secondary structures and then scanning the array after exposure to a given analyte.

BRIEF DESCRIPTION OF THE DRAWINGS

FIG. 1 is a schematic representation of a fabrication scheme for constructing multi-element DNA arrays according to the present invention. A clean gold surface is reacted with an amine-terminated alkanethiol and subsequently reacted with a protecting group to create a hydrophobic surface. This surface is then exposed to UV radiation through a quartz mask and rinsed with solvent to remove the alkanethiol+protecting group from specific areas of the surface, leaving bare gold pads. These bare gold areas on the sample surface are filled in with the alkanethiol, resulting in an array of alkanethiol pads surrounded by a hydrophobic protecting-group background. Solutions of nucelic acid are then delivered by pipette onto the specific array locations and are covalently bound to the surface via a bifunctional linker. In the final two steps, the protecting groups on the array background are removed and replaced by functional groups which prohibit the non-specific binding of analyte proteins to the background.

DETAILED DESCRIPTION OF THE INVENTION

Abbreviations and Commercial Suppliers

The following abbreviations and terms are used throughout the specification and claims. All other terms have their standard, accepted meaning in the relevant art.
"biomolecule"=any molecule found in biological material, expressly including, but not limited to nucleic acids, proteins, peptides, antibodies, enzymes, cell-wall components such as phospholipids, etc., and modified and synthetic forms thereof, such as labeled biomolecules and recombinant biomolecules.

"BSA"=bovine serum albumin (Sigma Chemical, St. Louis, Mo.).

"DMF"=dimethylformamide.

"Fmoc-NHS"=9-fluorenylmethoxycarbonyl-N-hydroxysuccinimide (Novabiochem, La Jolla, Calif.).

"metal substrate" or "metal film"=a noble-metal thin film (gold, silver, copper, platinum, etc.). Gold is preferred.

"MUAM"=11-mercaptoundecylamine (a generous gift from the laboratory of Professor George M. Whitesides, Harvard University, Boston, Mass.).

"NHSS"=N-hydroxysulfosuccinimide ester.

"nucleic acids"=deoxyribonucleic acids (DNA), ribonucleic acids (RNA), and peptide nucleic acids from any source, and modified forms thereof, including, without limitation, labeled (radioactive, fluorescent, etc.) nucleic acids, and nucleic acids modified to include a binding moiety such as a thiol group or a biotin tag.

"PEG"=poly(ethylene glycol).

"PEG-NHS"=N-hydroxysuccinimidyl ester of methoxypoly(ethylene glycol) propionic acid MW 2000 (Shearwater Polymers, Inc., Huntsville, Ala.).

"poly(ethylene glycol)-modified alkanethiol"=HS($CH_2$)$_{11}$(O$CH_2$$CH_2$)$_3$OH (from Dr. Whitesides' laboratory).

"SSB"=single-stranded DNA binding protein (Pharmacia Biotech, Piscataway, N.J.).

"SSMCC"=sulfosuccinimidyl 4-(N-maleimidomethyl) cyclohexane-1-carboxylate (Pierce Chemical, Rockford, Ill.).

"TAEA"=tris(2-aminoethyl)amine (Aldrich Chemical, Milwaukee, Wis.).

"TEA"=triethanolamine hydrochloride (Sigma)

"ω-modified alkanethiol"=an alkanethiol whose terminal carbon atom has been modified by the addition of a chemically-reactive moiety such as an amino, hydroxy, carboxy, or thiol moiety.

The above chemicals and were all used as received. Solvents were of standard laboratory grade and Millipore (Marlborough, Mass.) filtered water was used for all aqueous solutions and rinsing.

The chemical modification of a metal substrate to create a nucleic acid array thereon proceeds in seven general steps These steps are illustrated schematically in FIG. 1 and are as follows:

(1). Self-assembly of an ω-modified alkanethiol monolayer on a metal substrate. The ω-modification to the alkanethiol may be the addition of any moiety with enables further covalent linkages to be made the ω-terminus of the alkanethiol. Such modifications include, without limitation, the addition of an amine group, a hydroxyl group, a carboxyl group, or a thiol group to the ω carbon of the alkanethiol chain. The alkanethiol monolayer is preferably an amino-$C_8$–$C_{24}$-alkanethiol, a straight-chain alkane being much preferred to branched alkane; the most preferred ω-modified alkanethiol is MUAM.

(2). Reaction of the ω-modified alkanethiol surface with a hydrophobic protecting group, most preferably Fmoc.

(3). Photopatterning of the surface to create an array of bare metal areas.

(4). Re-assembly using additional (ω-modified alkanethiol to fill in the bare metal array elements, thereby yielding islands of ω-modified alkanethiol.

(5). Covalently attaching biomolecules or cells to the islands of ω-modified alkanethiol.

(6). Removal of the protecting group from the array background.

(7). Reaction of the background with a material, preferably PEG, to make the background resistant to non-specific protein binding. (The numbers in parentheses directly above are reference numerals in FIG. 1.)

To ensure the quality of the finished product, each of the above steps may be monitored using PM-FTIRRAS, contact angle measurements, and scanning-angle SPR.

Figure 1:
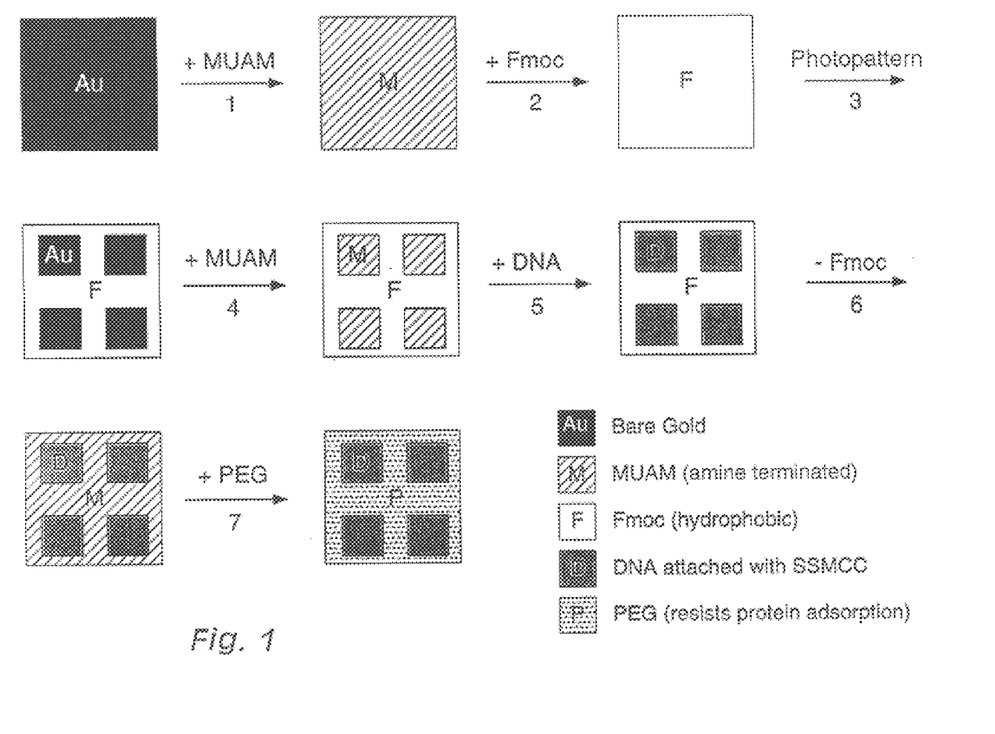

The above steps are now described in greater detail, with specific reference being made to FIG. 1.

Step (1). In step (1), a monolayer of ω-modified alkanethiol, preferably an amine-terminated alkanethiol, most preferably MUAM, is self-assembled from an ethanolic solution onto a silanized substrate (glass or other substrate transparent to the wavelengths of radiation to be used in subsequent analysis) coated with a thin noble-metal film. In the preferred embodiment, a film of gold about 450 Å thick is used. The thickness of the metal film is not overly critical insofar as the film is uniformly applied and will function in SPR imaging analysis. Self-assembled monolayers of ω-modified alkanethiols on gold have been described previously, see, for example, Thomas et al. (1995) *J Am. Chem. Soc.* 117:3830–3834, and are generally accepted by most to form well-ordered, monomolecular films. However, if left exposed for extended periods of time, the terminal amine groups of amino-modified alkanthiols will react with $CO_2$ to form carbamate salts on the surface. Consequently, amino-terminated alkanethiol-coated substrates should be handled with care and their exposure to $CO_2$ minimized.

Figure 3:
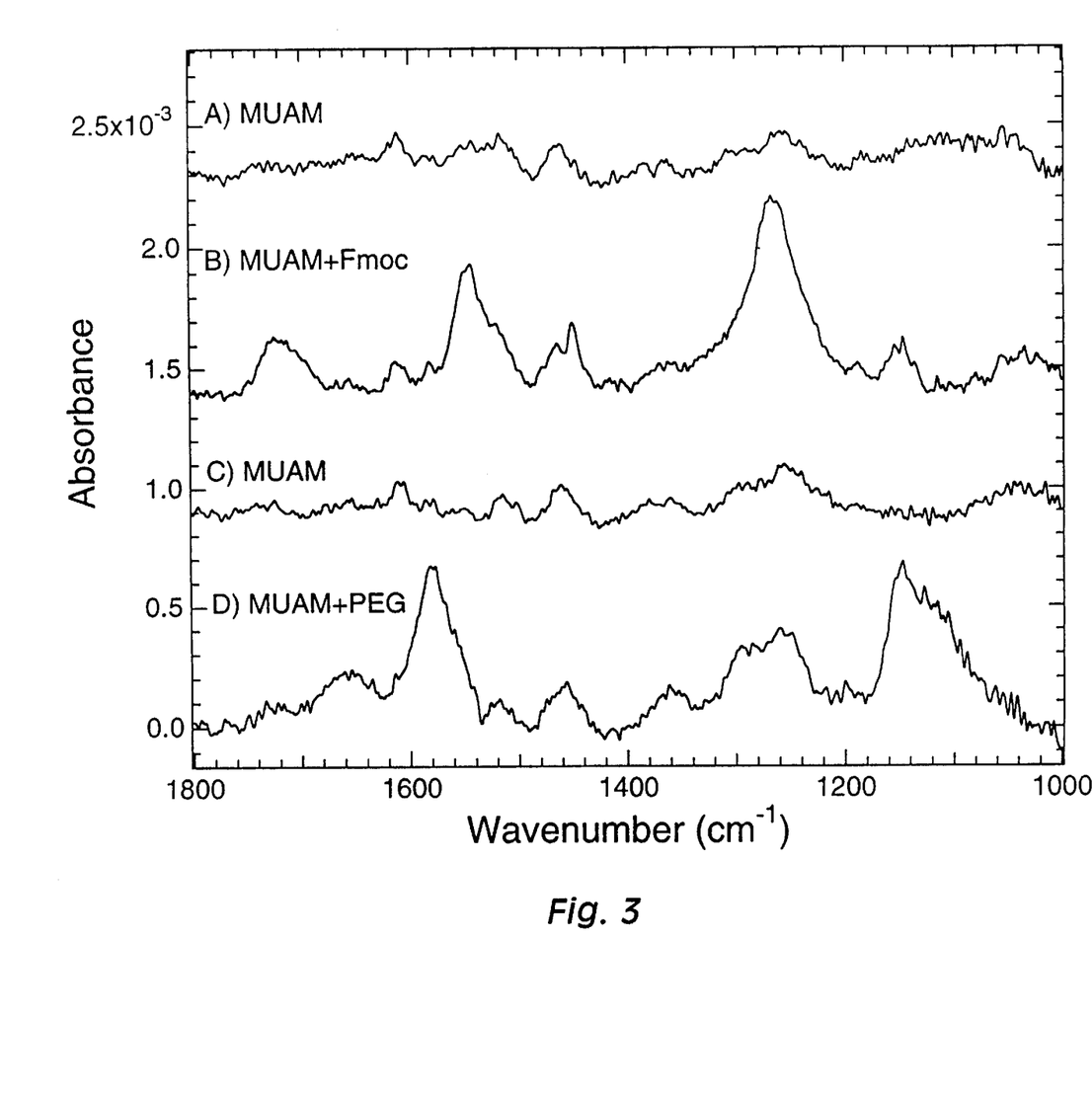
FIG. 3 depicts PM-FTIRRAS spectra in the mid-IR region for the surfaces involved in the array background modification. (A) The starting MUAM surface. (B) After reaction with Fmoc-NHS, bands indicative of the carbamate linkage and the Fmoc ring stretch appear in the spectrum. (C) The surface is deprotected and reverts back to the MUAM surface as evidenced by the similarities between spectra A and C. (D) After reaction with PEG-NHS, bands indicative of the amide linkage as well as those associated with the ethylene glycol groups are present.
Figure 4:
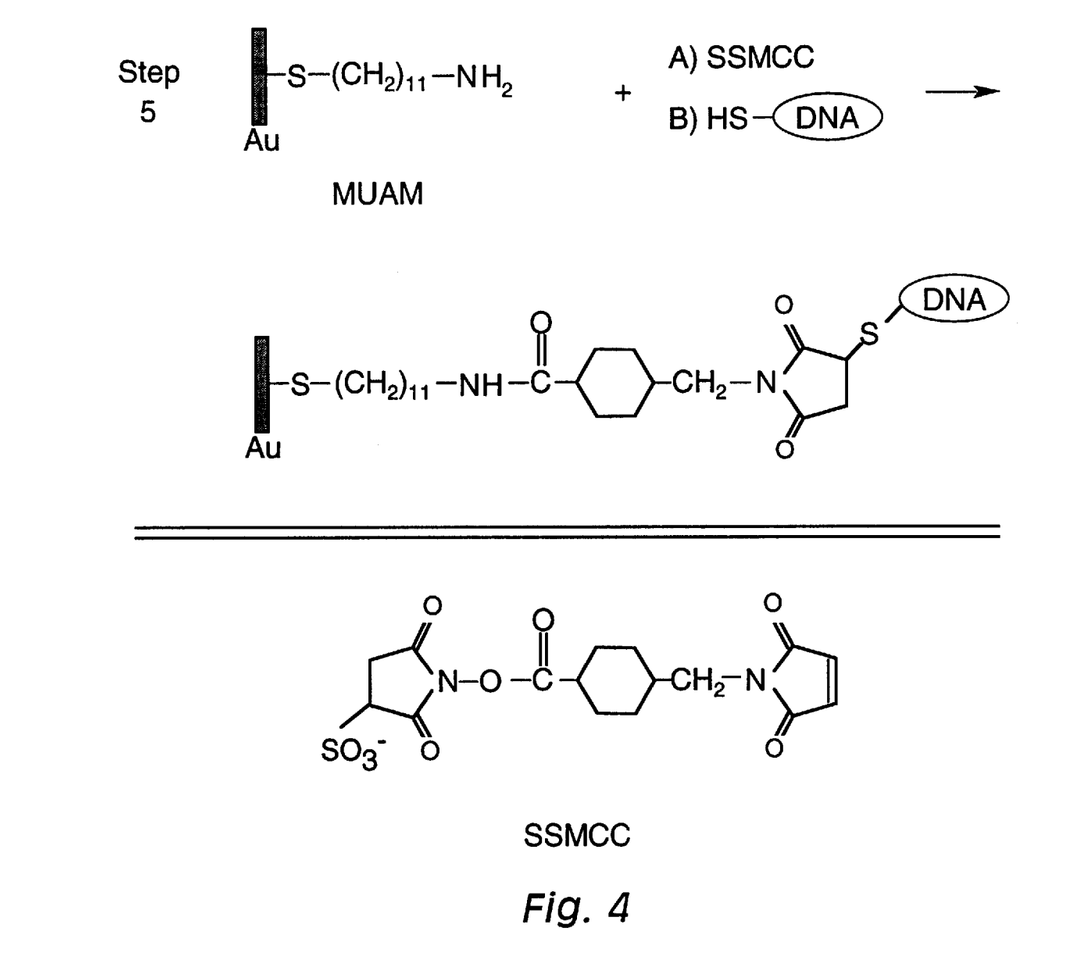
FIG. 4 depicts a surface reaction scheme showing the steps involved in immobilizing biomolecules, in this case DNA, to the array locations. A bifunctional linker, such as SSMCC, is used to link thiol-modified DNA to the MUAM pads.

The PM-FTIRRAS spectrum of MUAM in the mid-IR region is shown in FIG. 3, plot (A). The small peak centered at 1545 $cm^{-1}$ has been assigned as the $NH_3^+$deformation. The presence of this peak suggests that after a rinsing with ethanol and Millipore water (pH~6), a significant portion of the terminal amine groups exist in the protonated form. Variation in the intensity of the 1545 $cm^{-1}$ peak can be effected by rinsing the surface in solutions of differing pH. Bands at 1465 and 1258 $cm^{-1}$ in this same plot have been assigned to the $CH_2$ scissoring and twist deformations of the alkane chains respectively. The frequencies of the peaks due to the $CH_2$ asymmetric stretching mode at 2923 $cm^{-1}$ and the $CH_2$ symmetric stretching mode at 2853 $cm^{-1}$ (spectrum not shown) indicate that the monolayer exists in a relatively ordered state. Absent from the spectrum in the CH stretching region is a band due to the N-H stretch (~3200–3500 $cm^{-1}$) of the amine groups; it is assumed that this band is too weak to be detected. Due to its terminal amine groups, a MUAM monolayer surface is quite hydrophilic, which is verified by a contact angle measurement of 36.2±2.5 and is consistent with monolayer formation. Ex situ scanning SPR was used to measure a thickness of 17.5 Å±0.4 Å for a gold surface modified with MUAM; this thickness is consistent with that expected for a fully extended MUAM monolayer oriented nearly normal to the surface.

Step (2). In step (2) of the array fabrication, the MUAM covered surface is reacted with a reversible protecting group to create a hydrophobic surface. In the case of MUAM, an amine-modified alkanethiol, the protecting group is, appropriately, an amino protecting group, preferably Fmoc. Fmoc is a bulky, hydrophobic, base labile, amine protecting group routinely used in the solid phase synthesis of peptides.

The choice of protecting group used is dependent in large measure upon the nature of the ω-modification made to the alkanethiol. If the ω-modification is the addition of a carboxyl group, a hydrophobic carboxy protecting group would be used. Likewise, if the ω-modification is the addition of a hydroxyl or thiol group, a hydrophobic hydroxy or thiol protecting group, respectively, would be used. Any type of hydrophobic protecting suitable for protecting the ω-modification used on the alkanethiol can be utilized in the present invention. Numerous such protecting groups, for any number of reactive moieties, such as amine, hydroxy, and carboxy functionalities, are known to the art. For example, chloride derivatives of both Fmoc and trityl to can be used to reversibly modify hydroxyl-terminated alkanethiols.

Figure 2:
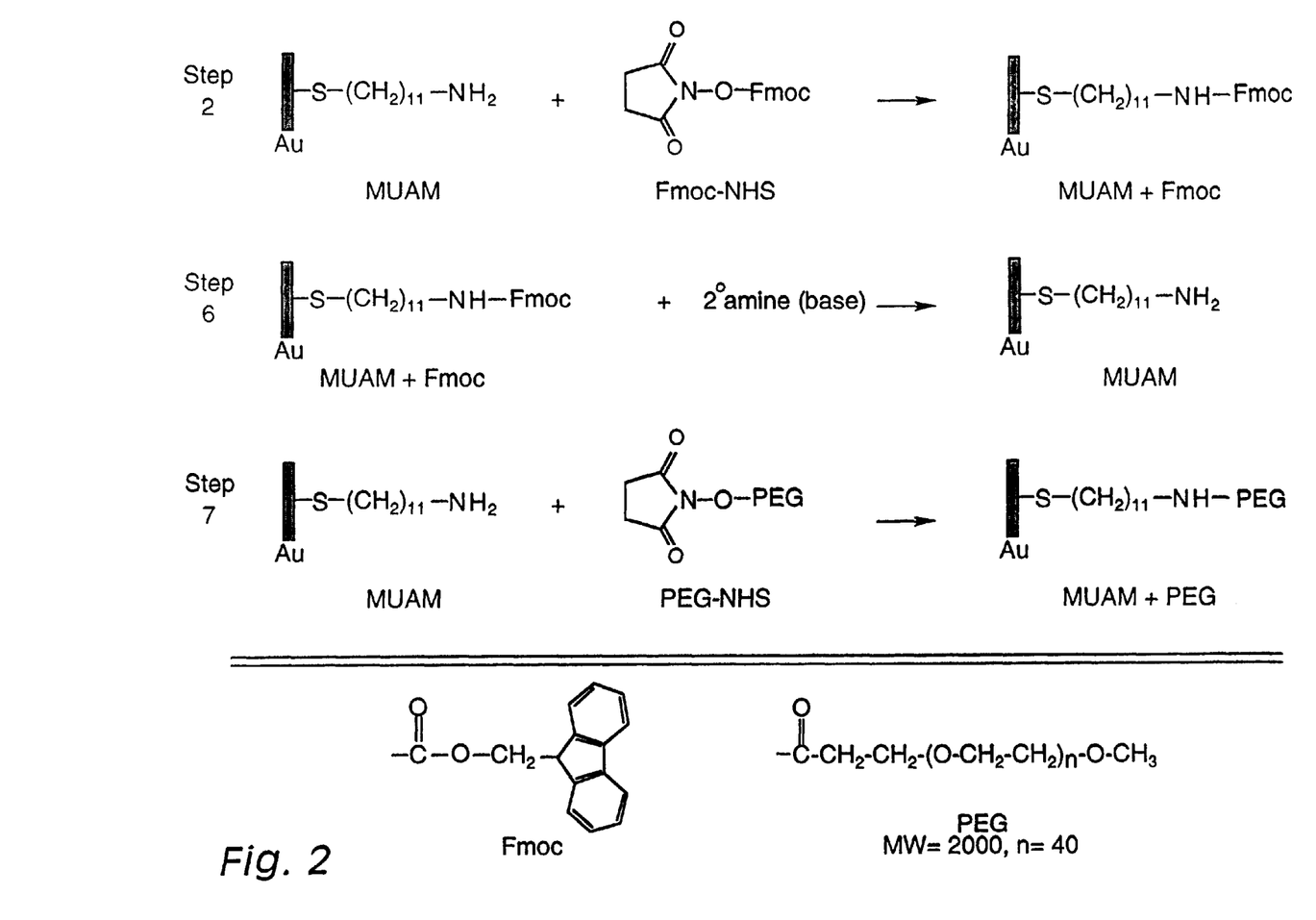
FIG. 2 depicts a surface reaction scheme showing the steps involved in the reversible modification of the array background. The starting amine-terminated alkanethiol surface is reacted with the Fmoc-NHS protecting group to form a carbamate linkage thus creating a hydrophobic Fmoc-terminated surface. After nucleic acid immobilization, the surface is deprotected, resulting in the return of the original alkanethiol surface. In the final array fabrication step, the deprotected alkanethiol surface is reacted with PEG-NHS to form an amide bond which covalently attaches PEG to the array surface (to prevent non-specific binding of analyte proteins to the background).

The specific chemical reaction for Fmoc is shown in FIG. 2, reference number (2). The N-hydroxysuccinimide ester of Fmoc (Fmoc-NHS) reacts with the terminal amine moiety of the MUAM molecule to form a stable carbamate (urethane) linkage, covalently attaching the Fmoc group to the surface. The IR spectrum of Fmoc linked to a MUAM-coated gold substrate is shown in FIG. 3, plot (B). This spectrum provides evidence that the surface reaction proceeds as expected. Prominent peaks at 1720, 1544, and 1267 $cm^{-1}$ are due to the carbamate (urethane) linkage which tethers the Fmoc group to the MUAM surface. (The band at 1720 $cm^{-1}$ has been assigned to the carbonyl stretching vibration (amide I), that at 1544 $cm^{-1}$ to the CHN group vibration, and that at 1267 $cm^{-1}$ to the coupled C—N and C—O stretches (amide IV).) The peak at 1450 $cm^{-1}$ is ascribed to the C=C ring stretch of the fluorenyl group and the band centered at 1147 $cm^{-1}$ is attributed to the Fmoc C—O—C (ether) stretch. After reaction with Fmoc-NHS, the surface properties of the array are changed significantly; the surface is extremely hydrophobic as confirmed by the measured contact angle of 74.4±2.5. In addition, an increase in the film thickness to 22.8 Å±0.5 Å is measured with scanning angle SPR.

Step (3). In step (3) the bond anchoring the ω-modified alkanethiol to the metal substrate is selectively cleaved to yield a patterned surface of exposed metal. UV photopatterning is preferred to create the patterned surface, although the means to create the patterned surface is not critical so long as the method reliable yields the desired pattern. For example, microcontact printing methods can also be used to yield a patterned surface. Using UV patterning, the surface is exposed through a quartz mask to UV radiation which photo-oxidizes the gold-sulfur bond that anchors the alkanethiol monolayers to the surface. The surface is then rinsed, removing the photo-oxidized alkanethiol and leaving an array of bare metal pads surrounded by a hydrophobic MUAM+Fmoc background. Using photopatterning, features with dimensions as small as 50 mm have been achieved; using microcontact printing methods, arrays with features as small as~100 nm are achievable.

Step (4). In step (4), the surface is again exposed to an ω-modified alkanethiol solution (in the preferred embodiment an ethanolic solution of MUAM) whereby the alkanethiol assembles into the bare gold regions producing a surface composed of hydrophilic MUAM pads surrounded by the hydrophobic Fmoc background. This difference in hydrophobicity between the reactive MUAM regions and the background is essential for the pinning of small volumes of aqueous biomolecule or cell solutions onto individual array locations.

Step (5). At step (5) in the process, biomolecules or cells (preferably nucleic acids) are then covalently attached to the surface. As illustrated, the MUAM reactive pads are first exposed to a solution of a bifunctional linker. To be used in the invention, the linker must be capable of binding at one end to the ω-modified alkanethiol surface and at the other end to the biomolecule or cell to be immobilized to form the desired array. Any bifunctional linker having these characteristics can be used in the present invention. The preferred bifunctional linker is SSMCC, a heterobifunctional linker which contains both an N-hydroxysulfosuccinimide (NHSS) ester and a maleimide functionality. The NHSS ester end of the molecule reacts with the free amine groups on an amino-modified surface, such as the MUAM spots, creating pads terminated in maleimide groups which are reactive towards thiols. Small volumes (0.08 to 0.1 L) of 1 mM solutions of 5'-thiol-modified DNA sequences are then spotted at discrete array locations and react to form a covalent attachment to the surface. See FIG. 2, reference numeral (5). Using this technique, a whole host of biomolecules and/or whole cells can be spotted at different array locations.

A variation on this attachment scheme whereby thiol-DNA is linked via SSMCC to a MUA/PL (11-mercaptoundecanoic acid/poly-L-lysine) bilayer has been used quite extensively in this laboratory, see U.S. Pat. No. 5,629,213. Other researchers have used the direct self-assembly of thiol-terminated DNA molecules on gold to prepare functionalized surfaces, but this method has the disadvantage that only weak forces exist for the self-assembly of oligonucleotide molecules and hence, the DNA can also non-specifically adsorb to the bare gold surface.

Here, a bifunctional linker is used to attach 5'-thiol-modified oligonucleotide sequences to reactive pads of aminoalkanethiol. The bifunctional linker preferably contains a functionality reactive towards amines and a functionality reactive towards aminoalkanethiols. The surface is first exposed to a solution of the linker, whereby one end of the molecule reacts with the aminoalkanethiol surface. Excess linker is rinsed away and the array surface is then spotted with 5'-thiol-modified nucleic acid which reacts with the other end of the bifunctional linker, forming a covalent bond between the nucleic acid and the surface monolayer.

Step (6). In step 6 the protecting group, depicted here as Fmoc is removed from the array surface. Preferably, this is accomplished by exposure to a 1M solution of the secondary amine, TAEA, in DMF. Many basic secondary amines can be used to remove Fmoc from the surface; for example, 1M solutions of ethanolamine and piperidine can be used with equal success. TAEA was chosen specifically as the deprotection agent since it effectively scavenges the dibenzofulvene byproduct and is efficiently rinsed from the array surface. After this deprotection step, the array background has been converted back to the original ω-modified alkanethiol surface. The spectrum of a deprotected MUAM surface, the preferred embodiment, is shown in FIG. 3, plot (C); note the strong similarity between it and the original MUAM spectrum. The prominent bands due to the carbamate linkage no longer appear, indicating that the Fmoc protecting group has been completely removed from the surface. The deprotected surface was also measured with scanning SPR; the thickness measured was within ±1 Å of that measured for the starting MUAM surface and this gives additional proof that the Fmoc protecting group is removed completely from the surface.

Step (7). In the final step of the array fabrication, the ω-modified alkanethiol background is reacted with a compound to create a background that is resistant to the non-specific binding of proteins. The preferred compound for this purpose is PEG-NHS, although any compound which will selectively bind to the ω-modified alkanethiol surface and inhibit non-selective protein binding can be used. In order to effectively monitor the binding of proteins to arrays of surface-bound biomolecules or cells, it is critical that the array background prohibit the non-specific adsorption of protein molecules. Significant amounts of such non-specific binding obscures the measurement of small amounts of protein binding at specific array locations.

To create a background that is resistant to the non-specific binding of proteins, the MUAM surface was reacted with PEG-NHS as is shown in FIG. 2 reference number (7). As was the case in the Fmoc-NHS+MUAM reaction, PEG-NHS reacts with the terminal amine groups of the MUAM to form an amide linkage, covalently attaching the PEG polymer chain to the surface. The preferred PEG-NHS polymer has an average molecular weight of 2000 and contains one NHS ester moiety per molecule, allowing for a single point of attachment. The spectrum collected for a MUAM surface reacted with PEG-NHS is shown in FIG. 3, plot (D). The peaks which appear at 1660 cm$^{-1}$ and 1576 cm$^{-1}$ have been assigned as amide I and II bands, respectively. The bands at 1457 cm$^{-1}$ and 1250–1260 cm$^{-1}$ are ascribed to the scissoring and twist deformations of the $CH_2$ groups contained in both the MUAM alkyl chains and the ethylene glycol (EG) groups. The band at 1352 cm$^{-1}$ is due to an EG $CH_2$ wagging mode, and the band centered at 1148 cm$^{-1}$ is due to the C—O—C (ether) stretch of the ethylene glycol units. After the reaction of the deprotected surface with PEG-NHS, the surface remains hydrophilic and has a measured contact angle of 37.3±2.6. A total thickness of 23.8 Å±0.8 Å was measured for a MUAM monolayer film after reaction with PEG-NHS. This increase of only 6 Å of PEG suggests that only a small fraction of the amine groups of the MUAM are modified and that the oligo(ethylene glycol) chains are lying flat across the surface.

An SPR imaging experiment (see Example 2 and FIG. 7) was used to measure the non-specific adsorption of BSA to a dual component surface ($C_{18}$-thiol/MUAM+PEG) and shows quite clearly that MUAM+PEG effectively resists the non-specific adsorption of proteins.

EXAMPLES

The following Examples are included solely to provide a more complete understanding of the present invention. The Examples do not limit the scope of the invention disclosed and claimed herein in any fashion.

Standard Procedures for All Examples

Gold substrates used in PM-FTIR and contact angle measurements were purchased commercially (Evaporated Metal Films) and those used in scanning or imaging SPR measurements were prepared by vapor deposition onto microscope slide covers that had been silanized with (3-mercaptopropyl)trimethoxysilane (Aldrich) in a manner similar to that reported by Goss et al. (1991) Anal. Chem. 63:85–88.

All oligonucleotides were synthesized on an ABI (Foster, Calif.) DNA synthesizer at the University of Wisconsin Biotechnology Center. Glen Research's (Sterling, Va.) "5'-Thiol-Modifier C6" and ABI's "6-FAM" were used for 5'-thiol-modified and 5'-fluorescein-modified oligonucleotides respectively, and "Spacer Phosphoramidite 18" (Glen Research) was used for the addition of an ethylene glycol spacer region. Thiol-modified oligonucleotides were deprotected as outlined by Glen Research's product literature. (Glen Research Corp. (1990) "User Guide to DNA Modification and Labeling"). Before use, each oligonucleotide was purified by reverse-phase binary gradient elution HPLC (Shimadzu (Columbia, Md.) "SCL-10AVP") and DNA concentrations were verified with an HP8452A UV-VIS spectrophotometer (Hewlett-Packard, Palo Alto, Calif.).

The sequences of the DNA molecules used in the SSB experiment of Example 1 were as follows:

D1=5'HS(CH$_2$)$_6$(T)$_{16}$AAC GAT GCA GGA GCA A (SEQ. ID. NO: 1)

D2=5'HS(CH$_2$)$_6$(CH$_2$CH$_2$O)$_{24}$GCT TAT CGA GCT TTC G (SEQ. ID. NO: 2)

D2 complement=5'FAM-CGA AAG CTC GAT AAG C (SEQ. ID. NO: 3)

The buffer used in the BSA and SSB SPR imaging experiments contained 20 mM phosphate, 100 mM NaCl, 1 mM EDTA, 1 mM DTT, and 5 mM MgCl$_2$ and was buffered at pH 7.4.

Multi-step array fabrication: A clean gold substrate was immersed in a 1 mM ethanolic solution of MUAM for at least one hour to allow for the adsorption and self-assembly of the aminoalkanethiol monolayer. The substrate was rinsed with ethanol and water, dried under a stream of N$_2$, and was then reacted with a solution of Fmoc-NHS (3 mM in 1:1 DMSO:100 mM TEA buffer, pH 7). The sample was soaked briefly in DMSO to remove unreacted Fmoc-NHS from the surface and then photopatterned by irradiating the sample with UV light from a mercury-xenon arc lamp through a quartz mask. Subsequent rinsing of the sample with ethanol and water removed alkanethiol from the exposed areas. The sample was re-exposed to the ethanolic MUAM solution resulting in an array of MUAM elements surrounded by a hydrophobic MUAM+Fmoc background. Single-stranded, 5'-thiol modified DNA was then immobilized onto the array locations using an attachment scheme modified slightly from that used previously. Briefly, the amine-terminated MUAM array elements were spotted with 0.1 µL of a 1 mM solution (in 100 mM TEA, pH 7) of the heterobifunctional linker SSMCC, creating a thiol-reactive, maleimide-terminated surface. 5'-Thiol-modified DNA sequences were then covalently attached to these maleimide-terminated array elements by spotting the sample with 0.1 µL drops of solutions containing 1 mM DNA onto the specific array locations and reacting for at least 2 hours in a humid environment to prevent solvent evaporation. After exposure to the DNA solution, the surface was rinsed with water and soaked in buffer to remove unbound DNA sequences. The Fmoc was then removed from the background by immersing the array in a 1M solution of TAEA in DMF for 10 minutes. The deprotected surface was rinsed with water and subsequently reacted with 4 mM PEG-NHS (in 100 mM TEA, pH 8) to pegylate the array background, rendering it resistant to protein non-specific binding.

PM-FT-IRRAS Measurements: PM-FT-IRRAS spectra were collected on a Mattson RS-1 spectrometer equipped with either a narrow band HgCdTe detector (for spectra in the mid-IR region, 2000-1000 cm$^{-1}$) or an InSb detector (for spectra in the CH stretching region, 3400-2600 cm$^{-1}$). The optical layout and previously developed real-time interferogram sampling methods have been described elsewhere and need not be elaborated upon here. The PM-FT-IRRAS differential reflectance values (% R/R) were converted to absorbance units for comparison with conventional IRRAS data. Spectra are an average of 1000 scans collected at 2 cm$^{-1}$ resolution.

Contact Angle Measurements: Water contact angles were determined at ambient laboratory temperatures using standard and well known procedures. Ten microliter droplets were dispensed from a Gilson pipette onto the surface and the angle measurement was recorded immediately. Reported contact angle values for both the Fmoc and PEG functionalized surfaces are the average of 12 different measurements taken on 4 individually prepared samples and the value for MUAM is the average of 30 measurements taken on 10 different samples.

Scanning Angle SPR Measurements: The optical technique of ex situ scanning SPR was used to determine the thickness (reported hereinabove) of MUAM, MUAM+Fmoc, and MUAM+PEG assembled on BK7 coverslips (Fisher Scientific, Pittsburgh, Pa.) onto which 475 Å of Au was vapor deposited. Details of the SPR experiment and thickness calculations have been reported elsewhere. Briefly, the reflectivity (R) of a p-polarized HeNe laser beam (632.8 nm) from a sample assembly (BK7 prism/Au/thin film/air) is monitored as a function of incident angle, to generate a SPR curve (% R vs. angle). A steep drop in the reflectivity occurs at angles just past the critical angle (~44). The exact position of the minimum is determined by the thickness and index of refraction of material adsorbed at the gold surface. A 4-phase complex Fresnel calculation was used to determine the film thickness and a refractive index of 1.45 was assumed for all the thin films measured here.

SPR Imaging Apparatus: The in situ SPR imaging instrument is a modified version of that described previously, see Jordan & Corn (1997) *Anal. Chem.* 69(7):1449–1456; Thiel et al. (1997) *Anal. Chem.* 69:4948–4956; Jordan et al. (1997) *Anal. Chem.* 69(24):4939–4947; and Frutos et al. (1998), supra, in which the HeNe laser and beam expander have been replaced by a collimated white light source/bandpass filter combination. A more thorough discussion of this modification in the context of near IR (NIR) SPR imaging is reported elsewhere, see Nelson et al. (1999), in preparation. In short, a collimated, polychromatic beam of light was used to illuminate an SF10 prism/Au/thin film/buffer assembly at a fixed incident angle near the SPR angle. The reflected light was passed through a 10 nm bandpass filter (830 nm) and was collected with an inexpensive CCD camera. Differences in the reflected light intensity measured at various locations on the sample create the image and are a direct result of differences in the thickness or refractive index of the material bound at the gold surface. The image shown in FIG. 6 was collected in situ for a sample constructed on SF10 substrates onto which 450 Å of Au had been deposited. Data work-up was done using NIH Image v.1.61 software.

EXAMPLE 1

Figure 6:
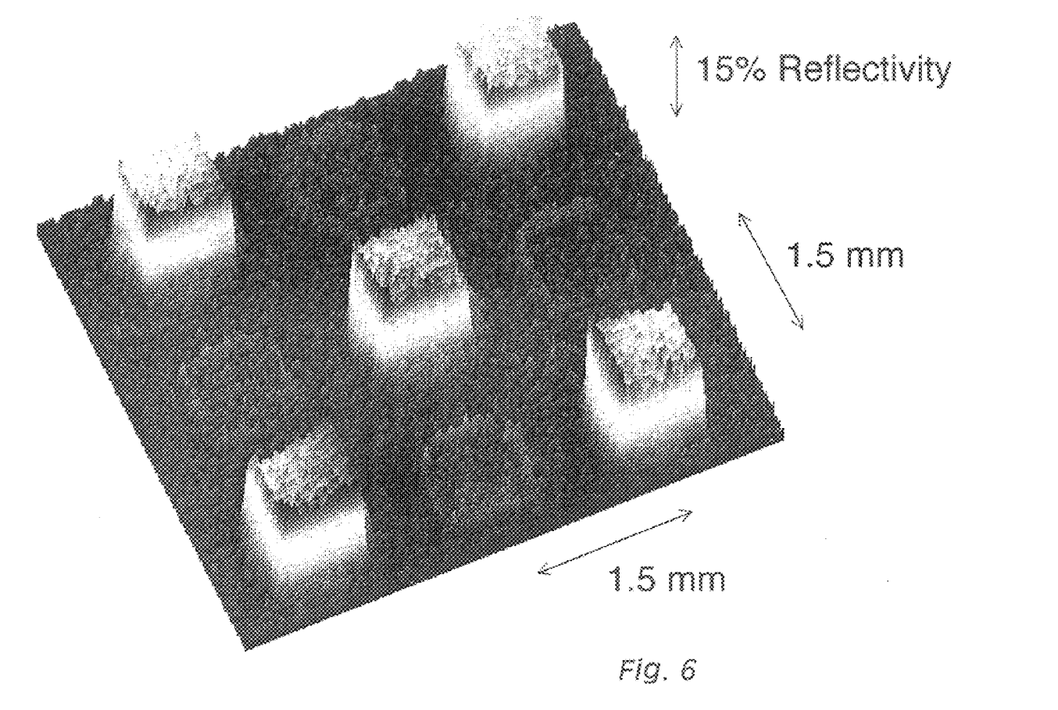
FIG. 6 depicts an in situ SPR difference image showing the binding of single stranded DNA binding protein (SSB) to a checkerboard array of single- and double-stranded oligonucleotide sequences. Images collected immediately before and after exposure of the surface to SSB were subtracted to produce the image shown. Significant binding of the protein to array locations with covalently bound single-stranded DNA sequences occurred, whereas very little binding occurred at the array locations which contained double-stranded DNA sequences.

SPR imaging measurements of the binding of single stranded DNA binding protein to arrays of single and double-stranded DNA sequences To demonstrate that nucleic arrays can be used in conjunction with imaging SPR to monitor protein-nucleic acid binding, a checkerboard surface was constructed containing both single-stranded DNA (D1, SEQ. ID. NO: 1) and double-stranded DNA (D2 and its complement, SEQ. ID. NOS. 2 and 3, respectively), by the methods described immediately above. The binding of single-stranded DNA binding protein, SSB, to the array surface was then monitored by SPR. As its name implies, SSB (a tetramer of four identical subunits with a total molecular weight of 75,000 D) binds tightly, selectively, and cooperatively to single-stranded DNA and plays a central role in DNA replication, repair, and recombination. FIG. 6 shows the difference between two images collected immediately before and after the exposure of the surface to SSB. The raised areas on the image are a measure of the change in % R upon adsorption of the protein to the surface. The array locations at which the protein bound correspond to those regions which were modified with single-stranded DNA sequences.

Figure 5:
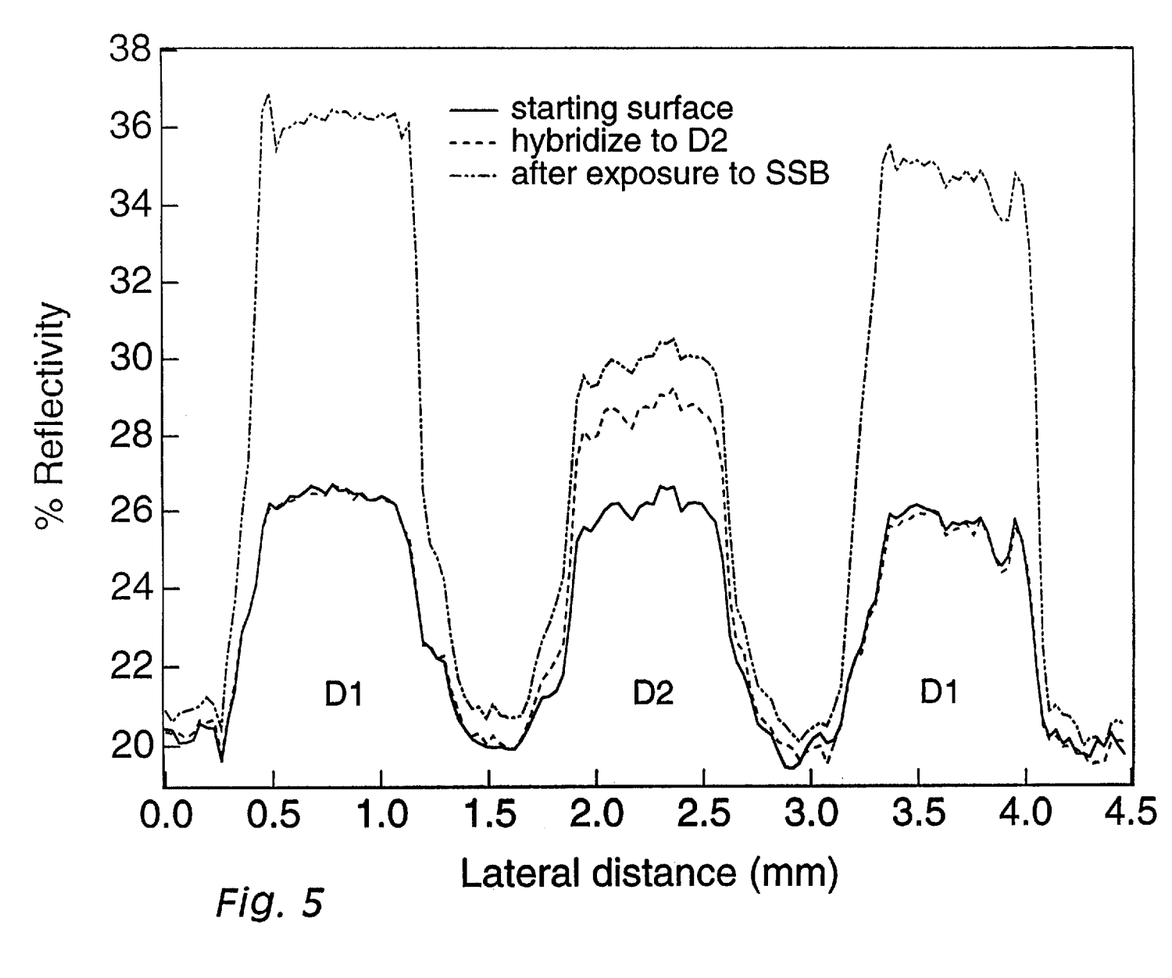
FIG. 5 depicts a series of line profiles showing in situ hybridization and the adsorption of single stranded DNA binding protein (SSB) onto a dual component DNA array containing oligonucleotide sequences D1 and D2. The solid line is the percent reflectivity measured for the starting surface composed of alternating DNA probe spots D1 and D2. The dashed line is the % R measured after exposing the surface to a solution containing the complement to D2. Apparent is an increase in % R at position D2 upon binding of the complementary DNA sequence. The dot-dashed line is the % R measured after exposing the surface to a 200 nM solution of SSB. While measurable binding did occur at array location D2 (which contained double stranded DNA), the protein clearly bound more abundantly to the single-stranded sequence D1.

FIG. 5 shows various line profiles taken from images collected during the course of the experiment. These "line profiles," which provide quantitative information, are constructed by averaging the % R values measured for each column of pixels in a selected rectangular region drawn across the image and then plotting this average value against that column's lateral position. The solid line shows the starting surface in which two 5'-thiol-modified, single-stranded DNA sequences, D1 and D2, were immobilized in a checkerboard pattern onto the array surface. The sequences of these two DNA probe strands are noted above. Each sequence contains a 5'-thiol modifier, a spacer region, and a 16 base-long variable sequence. The variable regions were specifically chosen from a library developed for the purposes of DNA computing, Frutos et al. (1997) supra, they and their complements exhibit no cross hybridization. To position the DNA sufficiently far from the surface so that stearic hindrance does not interfere with the hybridization adsorption process, a spacer region is incorporated. A 15T spacer region was used for D1, but sequence D2 contained a similar length EG spacer instead. This was necessary given the fact that SSB is known to bind quite strongly to polyT sequences. The dashed line shows the effects of exposing the surface, in situ, to a solution containing the 16-mer complement to D2 (SEQ. ID. NO: 3). A measurable change in % R occurred at location D2, indicating that hybridization adsorption of the complementary sequence took place; no increase in signal was seen at the D1 locations. The dot-dashed line shows the surface after exposure to a 200 nM solution of SSB. As expected, the protein bound strongly to locations on the array which were single stranded but also bound slightly to those locations that contained double-stranded sequences. Since SSB does not bind to double-stranded DNA, we attribute the increased signal at location D2 to the binding of SSB to single-stranded DNA present at these locations as a result of incomplete hybridization. It is important to note that the array background successfully resisted the non-specific binding of both complementary DNA molecules and single-stranded binding protein; this allows the measurement of small changes in % R without interference from a high background signal.

This Example shows that the arrays fabricated according to the present invention can be used to probe nucleic acid-protein interactions.

EXAMPLE 2

Demonstration that PEG block non-specific protein binding

Figure 7:
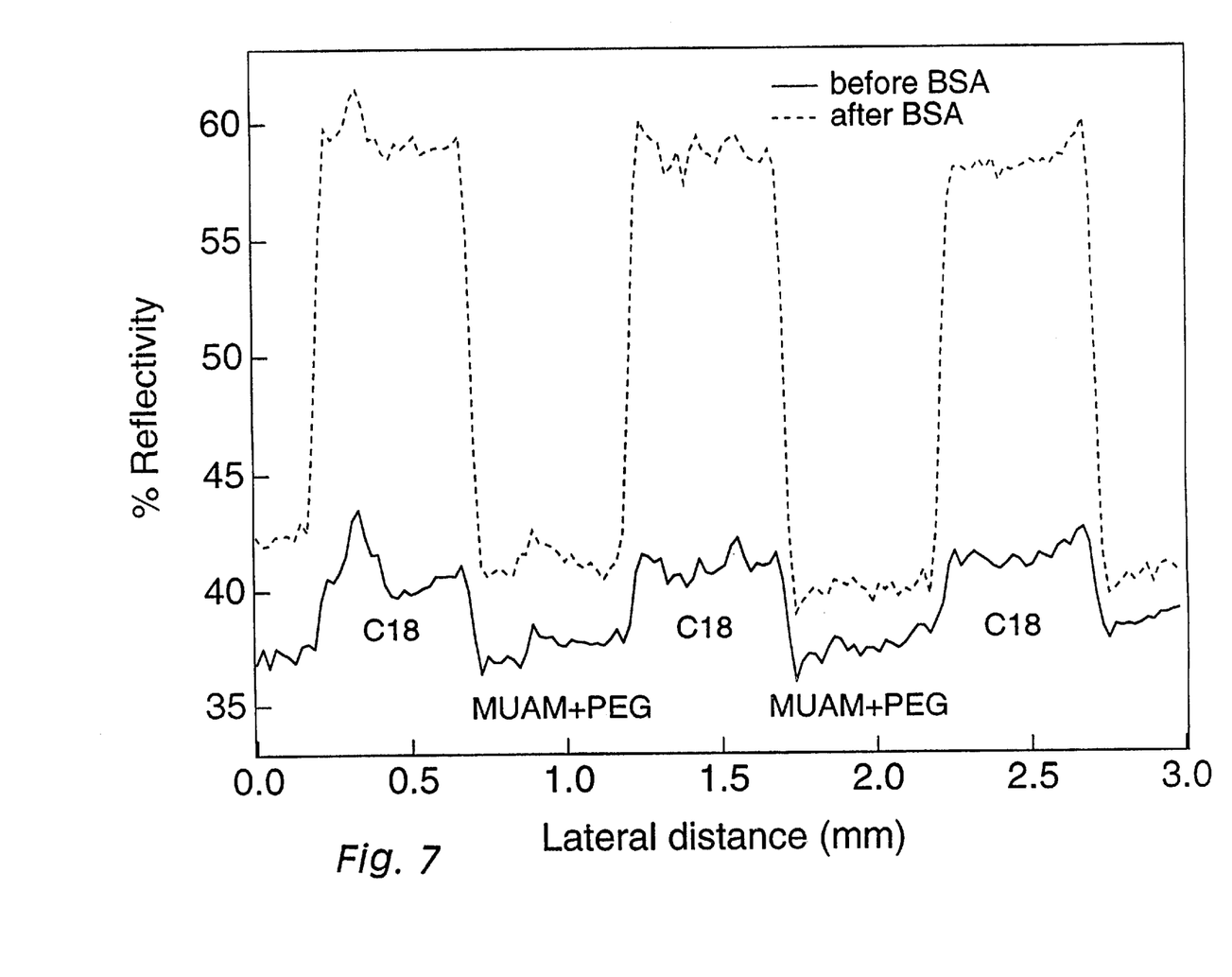
FIG. 7 depicts a series of line profiles showing the in situ adsorption of bovine serum albumin (BSA) onto a patterned $C_{18}$/MUAM+PEG surface. The solid line is the % R measured for a surface array of 350 mm spots of $C_{18}$ surrounded by a pegylated MUAM background. The dotted line is the % R measured after exposing the surface to a 1 mg/mL solution of BSA. The much lower change in % R for the MUAM-PEG regions indicates that the pegylated background is much more efficient than $C_{18}$ in resisting the non-specific binding of the BSA.

Here, an array of $C_{18}$ alkanethiol spots were assembled on a MUAM+PEG background using the techniques described above. The array was then exposed to BSA and the percent reflectivity measured as described in Example 1. The results are shown in FIG. 7. In FIG. 7, the solid line shows the percent reflectivity of the array prior to exposure to BSA. The dashed line shows the presence reflectivity after exposure to BSA.

While some BSA did adsorb to the MUAM+PEG background, a vastly large amount of BSA adsorbed to the untreated $C_{18}$ spots. This Example thus shows that PEG can be used to inhibit the non-specific binding of proteins to the background surface.

What is claimed is:

1. A method of making a biomolecule or cellular array on a metal substrate comprising:

(a) depositing an ω-modified alkanethiol monolayer on a metal substrate;

(b) reacting hydrophobic protecting groups with the monolayer;

(c) patterning the monolayer to create an array of exposed metal substrate areas;

(d) depositing ω-modified alkanethiol in the areas of exposed metal substrate, thereby yielding an array of discrete, unprotected ω-modified alkanethiol spots;

(e) attaching biomolecules or cells to the discrete, unprotected ω-modified alkanethiol spots, thereby yielding an array of discrete spots having biomolecules or cells immobilized thereon;

(f) removing the protecting groups of step (b); and then (g) making the monolayer resistant to non-specific protein binding wherein the method results in a biomolecule or cellular array.

2. The method of claim 1, wherein in step (a), an amino-$C_8$–$C_{24}$-alkanethiol is deposited on the metal substrate.

3. The method of claim 1, wherein in step (a), 11-mercaptoundecylamine is deposited on the metal substrate.

4. The method of claim 1, wherein in step (b), 9-fluorenylmethoxycarbonyl-N-hydroxysuccinimide is reacted with the monolayer.

5. The method of claim 1, wherein in step (c), the monolayer is patterned by selective exposure to UV radiation.

6. The method of claim 1, wherein in step (d), 11-mercaptoundecylamine is deposited in the areas of exposed metal substrate.

7. The method of claim 1, wherein in step (e), nucleic acid molecules are attached to the discrete, unprotected ω-modified alkanethiol spots using a bifunctional linker.

8. The method of claim 1, wherein in step (e), DNA molecules are attached to the discrete, unprotected ω-modified alkanethiol spots.

9. The method of claim 1, wherein in step (e), RNA molecules are attached to the discrete, unprotected ω-modified alkanethiol spots.

10. The method of claim 1, wherein in step (e), a hetero-bifunctional linker is used.

11. The method of claim 10, wherein in step (e), sulfosuccinimidyl 4-(N-maleimidomethyl)cyclohexane-1-carboxylate is used as a linker.

12. The method of claim 1, wherein in step (f), the protecting groups are removed by treating the monolayer with a secondary amine.

13. The method of claim 12, wherein in step (f), the protecting groups are removed by treating with a solution selected from the group consisting of tris(2-aminoethyl) amine, ethanolamine, and piperidine.

14. The method of claim 1, wherein in step (g), the monolayer is made resistant to non-specific protein binding by attaching poly(ethylene glycol) moieties thereto.

15. The method of claim 1, wherein in step (a) the ω-modified alkanethiol monolayer is deposited on a gold substrate.

16. The method of claim 15, wherein in step (a), an amino-$C_8$–$C_{24}$-alkanethiol is deposited on the gold substrate.

17. The method of claim 15, wherein in step (a), 11-mercaptoundecylamine is deposited on the gold substrate.

18. The method of claim 15, wherein in step (b), 9-fluorenylmethoxycarbonyl-N-hydroxysuccinimide is reacted with the monolayer.

19. The method of claim 15, wherein in step (c), the monolayer is patterned by selective exposure to UV radiation.

20. The method of claim 15, wherein in step (d), 11-mercaptoundecylamine is deposited in the areas of exposed gold substrate.

21. The method of claim 15, wherein in step (e), nucleic acid molecules are attached to the discrete, unprotected ω-modified alkanethiol spots using a bifunctional linker.

22. The method of claim 15, wherein in step (e), a heterobifunctional linker is used.

23. The method of claim 22, wherein in step (e), sulfosuccinimidyl 4-(N-maleimidomethyl)cyclohexane-1-carboxylate is used as a linker.

24. The method of claim 15, wherein in step (f), the protecting groups are removed by treating the monolayer with a secondary amine.

25. The method of claim 15, wherein in step (g), the monolayer is made resistant to non-specific protein binding by attaching PEG moieties thereto.

* * * * *

UNITED STATES PATENT AND TRADEMARK OFFICE
CERTIFICATE OF CORRECTION

PATENT NO.   : 6,127,129
DATED        : October 3, 2000
INVENTOR(S)  : Corn et al.

It is certified that error appears in the above-identified patent and that said Letters Patent is hereby corrected as shown below:

Column 1,
Line 13, before "FIELD OF THE INVENTION" please insert the following:
-- FEDERAL FUNDING
   This invention was made with United States government support awarded by the following agency: NSF 9626607. The United States has certain rights in this invention. --

Signed and Sealed this

Sixth Day of July, 2004

JON W. DUDAS
*Acting Director of the United States Patent and Trademark Office*